(12) United States Patent
Jacks et al.

(10) Patent No.: US 7,514,207 B2
(45) Date of Patent: Apr. 7, 2009

(54) METHODS OF SCREENING FOR COMPOUNDS THAT DECREASE PHOSPHORYLATION OF MERLIN AND MAY BE USEFUL IN CANCER TREATMENT

(75) Inventors: Tyler E. Jacks, West Newton, MA (US); Joseph L. Kissil, Wynnewood, PA (US)

(73) Assignee: Massachusetts Institute of Technology, Cambridge, MA (US)

( * ) Notice: Subject to any disclaimer, the term of this patent is extended or adjusted under 35 U.S.C. 154(b) by 242 days.

(21) Appl. No.: 10/486,750

(22) PCT Filed: Aug. 13, 2002

(86) PCT No.: PCT/US02/25568

§ 371 (c)(1),
(2), (4) Date: Dec. 3, 2004

(87) PCT Pub. No.: WO03/016328

PCT Pub. Date: Feb. 27, 2003

(65) Prior Publication Data

US 2005/0080002 A1 Apr. 14, 2005

Related U.S. Application Data

(60) Provisional application No. 60/311,873, filed on Aug. 13, 2001.

(51) Int. Cl.
*C12Q 1/00* (2006.01)
*C12Q 1/68* (2006.01)
*G01N 33/53* (2006.01)
*C07H 21/04* (2006.01)
*C07K 16/00* (2006.01)

(52) U.S. Cl. ............................. 435/4; 435/6; 435/7.1; 536/24.5; 530/387.1

(58) Field of Classification Search ...................... None
See application file for complete search history.

(56) References Cited

U.S. PATENT DOCUMENTS 5,698,445 A * 12/1997 Abo et al. .................... 435/325
6,013,500 A    1/2000 Minden

FOREIGN PATENT DOCUMENTS

WO    WO 99/02701    1/1999

OTHER PUBLICATIONS

Bocchetta et al. Oncogene 2004, vol. 23, pp. 6484-6491.*
Opalinska et al. Nature Reviews Drug Discovery, 2002, vol. 1, p. 503-514.*
Bumcrot et al. Nature Chemical Biology 2006, vol. 2, pp. 711-719.*
Zeng et al. Journal of Cell Science 2000, vol. 113, pp. 471-482.*
Adam et al., "Regulation of Microfilament Reorganization and Invasiveness of Breast Cancer Cells by Kinase Dead p21-activated Kinase-1," *The Journal of Biological Chemistry* 275:12041-12050 (2000).
Bargmann et al., "Increased Tyrosine Kinase Activity Associated With the Protein Encoded by the Activated Neu Oncogene," *Proceedings of the National Academy of Sciences of the U.S.A* 85:5394-5398 (1988).
Chong et al., "The Mechanism of PAK Activation: Autophosphorylation Events in Both Regulatory and Kinase Domains Control Activity," *The Journal of Biological Chemistry* 276:17347-17353 (2001).
del Pozo et al., "Adhesion to the Extracellular Matrix Regulates the Coupling of the Small GTPase Rac to its Effector PAK," *The EMBO Journal* 19:2008-2014 (2000).
Giovannini et al., "Conditional Biallelic Nf2 Mutation in the Mouse Promotes Manifestations of Human Neurofibromatosis Type 2," *Genes & Development* 14:1617-1630 (2000).
Joneson et al., "RAC Regulation of Actin Polymerization and Proliferation by a Pathway Distinct From Jun Kinase," *Science* 274:1374-1376 (1996).
Kissil et al., "Merlin Phosphorylation by p21-activated Kinase 2 and Effects of Phosphorylation on Merlin Localization," *The Journal of Biological Chemistry* 277:10394-10399 (2002).
Lamarche et al., "Rac and Cdc42 Induce Actin Polymerization and G1 Cell Cycle Progression Independently of p65$^{PAK}$ and the JNK/SAPK MAP Kinase Cascade," *Cell* 87:519-529 (1996).
Lamb et al., "The TSC1 Tumour Suppressor Hamartin Regulates Cell Adhesion Through ERM Proteins and the GTPase Rho," *Nature Cell Biology* 2:281-287 (2000).
Maruta et al., "Cytoskeletal Tumor Suppressors That Block Oncogenic RAS Signaling," *Annals of the New York Academy of Sciences* 886:48-57 (1999).
Pearson et al., "Structure of the ERM Protein Moesin Reveals the FERM Domain Fold Masked by an Extended Actin Binding Tail Domain," *Cell* 101:259-270(2000).
Rudel et al., "p21-activated Kinase (PAK) Is Required for Fas-Induced JNK Activation in Jurkat Cells," *Journal of Immunology* 160:7-11 (1998).
Sainio et al., "Neurofibromatosis 2 Tumor Suppressor Protein Colocalizes With Ezrin and CD44 and Associates with Actin-Containing Cytoskeleton," *Journal of Cell Science* 110:2249-2260 (1997).
Shaw et al., "Regulation of the Neurofibromatosis Type 2 Tumor Suppressor Protein, Merlin, by Adhesion and Growth Arrest Stimuli," *The Journal of Biological Chemistry* 273:7757-7764 (1998).
Shaw et al., "The Nf2 Tumor Suppressor, Merlin, Functions in Rac-Dependent Signaling," *Developmental Cell* 1:63-72 (2001).
Westwick et al., "Rac Regulation of Transformation, Gene Expression, and Actin Organization by Multiple, PAK-Independent Pathways," *Molecular and Cellular Biology* 17:1324-1335 (1997).
Vadlamudi et al., "Regulatable Expression of p21-activated Kinase-1 Promotes Anchorage-independent Growth and Abnormal Organization of Mitotic Spindles in Human Epithelial Breast Cancer Cells," *The Journal of Biological Chemistry* 275:36238-36244 (2000).
International Search Report mailed Dec. 17, 2002 (PCT/US02/25568).

* cited by examiner

*Primary Examiner*—Tracy Vivlemore
(74) *Attorney, Agent, or Firm*—Clark & Elbing LLP; Kristina Bieker-Brady

(57) ABSTRACT

The present inventions features methods for treating or preventing cancer (e.g., cancer of the central nervous system) by administering a compound that inhibits PAK kinase activity and/or merlin phosphorylation to a mammal (e.g., a human). The invention also provides screening methods for identifying additional inhibitors of PAK kinase activity and/or merlin phosphorylation.

18 Claims, 5 Drawing Sheets

SEQUENCE LISTING

<160> NUMBER OF SEQ ID NOS: 9

<210> SEQ ID NO 1
<211> LENGTH: 35
<212> TYPE: DNA
<213> ORGANISM: Artificial sequence
<220> FEATURE:
<223> OTHER INFORMATION: synthetic

<400> SEQUENCE: 1
ccaggaattc cattgccacc aagcccacgt acccg         35

<210> SEQ ID NO 2
<211> LENGTH: 36
<212> TYPE: DNA
<213> ORGANISM: Artificial sequence
<220> FEATURE:
<223> OTHER INFORMATION: synthetic

<400> SEQUENCE: 2
gcaagcatct gcaggagcag ctcgactcga gcggcc         36

<210> SEQ ID NO 3
<211> LENGTH: 33
<212> TYPE: DNA
<213> ORGANISM: Artificial sequence
<220> FEATURE:

-continued

<223> OTHER INFORMATION: synthetic

<400> SEQUENCE: 3
gcagagcaaa cgcagtgaga tggtcggaac gcc          33

<210> SEQ ID NO 4
<211> LENGTH: 33
<212> TYPE: DNA
<213> ORGANISM: Artificial sequence
<220> FEATURE:
<223> OTHER INFORMATION: synthetic

<400> SEQUENCE: 4
ggcgttccga ccatctcact gcgtttgctc tgc          33

<210> SEQ ID NO 5
<211> LENGTH: 30
<212> TYPE: DNA
<213> ORGANISM: Artificial sequence
<220> FEATURE:
<223> OTHER INFORMATION: synthetic

<400> SEQUENCE: 5
ccgctcgaga tgcacaccat ccatgttggc              30

<210> SEQ ID NO 6
<211> LENGTH: 34
<212> TYPE: DNA
<213> ORGANISM: Artificial sequence
<220> FEATURE:
<223> OTHER INFORMATION: synthetic

<400> SEQUENCE: 6
gctctagatt aatctttctc aggaggagta aagc         34

<210> SEQ ID NO 7
<211> LENGTH: 14
<212> TYPE: PRT
<213> ORGANISM: Artificial sequence
<220> FEATURE:
<223> OTHER INFORMATION: synthetic
<220> FEATURE:
<221> NAME/KEY: MOD_RES
<222> LOCATION: (10)..(10)
<223> OTHER INFORMATION: PHOSPHORYLATION

<400> SEQUENCE: 7

Cys Lys Asp Thr Asp Met Lys Arg Leu Ser Met Glu Ile Glu
1               5                   10

<210> SEQ ID NO 8
<211> LENGTH: 6
<212> TYPE: PRT
<213> ORGANISM: Artificial sequence
<220> FEATURE:
<223> OTHER INFORMATION: synthetic

<400> SEQUENCE: 8

Arg Lys Arg Leu Ser Gln
1               5

<210> SEQ ID NO 9
<211> LENGTH: 6
<212> TYPE: PRT
<213> ORGANISM: Artificial sequence
<220> FEATURE:
<223> OTHER INFORMATION: synthetic

```
<400> SEQUENCE: 9

Met Lys Arg Leu Ser Met
1               5
```

METHODS OF SCREENING FOR COMPOUNDS THAT DECREASE PHOSPHORYLATION OF MERLIN AND MAY BE USEFUL IN CANCER TREATMENT

CROSS-REFERENCE TO RELATED APPLICATIONS

This application is the National Stage of International Application No. PCT/USO2/25568, filed August 13, 2002, which was published in English under PCT Article 2 1(2), which claims benefit of U.S. Provisional Application No. 60/311,873, filed Aug. 13, 2001, each of which is hereby incorporated by reference.

BACKGROUND OF THE INVENTION

Neurofibromatosis type 2 is an inherited disorder characterized by the development of Schwann cell tumors of the eighth cranial (auditory) nerve. Mutations and loss of heterozygosity of the NF2 locus have been detected in various familial and sporadic tumors of the nervous system, including schwannomas, meningiomas, and ependymomas. These mutations have been detected both in the germ-line of Nf2 patients and sporadically occurring tumors, indicative of a classical tumor suppressor gene pattern. Together, these tumors account for approximately 30% of central nervous system neoplasms in adults. In further support of a role for NF2 in tumor suppression, mice heterozygous for a Nf2 mutation are predisposed to a wide variety of tumors with high metastatic potential. In a separate model in which Nf2 was inactivated specifically in Schwann cells, mice developed schwannomas and Schwann cell hyperplasia.

The longest and predominant splice form of the Nf2 gene codes for a 595-amino acid protein called merlin that is highly similar to the band 4.1 family of proteins. It is most closely related to the ERM proteins—ezrin, radixin, and moesin. The ERM proteins are thought to function as cell membrane-cytoskeleton linkers and are localized to cortical actin structures near the plasma membrane such as microvilli, membrane ruffles, and lamellipodia. Likewise, merlin is localized to cortical actin structures in patterns that partially overlap with the ERMs. It has been proposed that intramolecular binding of the N-terminal and C-terminal domains conformationally regulates the ERM proteins by masking binding sites for interacting proteins. The ERMs can also form homo-dimers and hetero-dimers among themselves and with merlin, adding an additional level of complexity to the regulation of these proteins. The recently solved crystal structure of moesin N/C-terminal complex strengthens this model of conformational regulation.

Unfortunately, many of the current treatments that destroy cancerous cells also affect normal cells, resulting in a variety of possible side-effects, such as nausea, vomiting, low blood cell counts, increased risk of infection, hair loss, and ulcers in mucous membranes. Thus, improved methods are needed for the treatment and prevention of cancers, such as cancers of the nervous system.

SUMMARY OF THE INVENTION

In general, the invention provides novel methods for the treatment or prevention of cancer (e.g., cancer of the central nervous system) by administering one or more compounds that inhibit PAK kinase activity and/or phosphorylation of merlin. Exemplary diseases that can be treated or prevented using these methods include neurofibromatosis type 2 or any other disease that involves aberrations in the function of the Nf2 gene or in the function of merlin.

In one aspect, the invention provides a method of treating, stabilizing, or preventing cancer in a mammal (e.g., a human) that involves reducing PAK kinase activity in the mammal. In desirable embodiments, a compound that reduces PAK kinase activity (e.g., PAK1, PAK2, PAK3, PAK4, PAK5, and/or PAK6 kinase activity) is administered to the mammal in an amount sufficient to treat, stabilize, or prevent cancer in the mammal. Desirably, an activity of a PAK kinase is reduced by at least 5, 10, 20, 30, 40, 50, 60, or 80, 90, 95, or 100%. In various embodiments, the compound is a purified or unpurified synthetic organic molecule, naturally occurring organic molecule, nucleic acid molecule, PAK kinase antisense nucleic acid or double stranded RNA molecule, biosynthetic protein or peptide, naturally occurring peptide or protein, PAK kinase antibody, or dominant negative PAK kinase protein (e.g., a mutant or fragment of a PAK kinase). In other embodiments, the compound is an autoinhibitory region of a PAK kinase, such as a protein that includes or consists of at least 25, 50, 75, 100, 125, or 150 contiguous amino acids of residues 82-146 of PAK2 or the corresponding region in another PAK kinase (e.g., residues 83-149 of PAK1). In certain embodiments, the protein includes at least 25, 50, 75, 100, 125, 150, 200, or 300 of the N-terminal amino acids of a PAK kinase. In some embodiments, the compound is staurosporine or an ATP analog.

In another aspect, the invention provides a method of treating, stabilizing, or preventing cancer in a mammal (e.g., a human) that involves reducing the amount of merlin that is phosphorylated (e.g., phosphorylation on serine 518) in the mammal. In desirable embodiments, a compound that reduces the phosphorylation level of merlin (e.g., phosphorylation at serine 518) is administered to the mammal in an amount sufficient to treat, stabilize, or prevent cancer in the mammal. In other desirable embodiments, the amount of merlin that is phosphorylated at serine 518 is reduced by at least 5, 10, 20, 30, 40, 50, 60, or 80, 90, 95, or 100%. In various embodiments, at least 20, 40, 50, 60, 80, 90, or 95% of merlin is located in microvilli. Exemplary merlin proteins have an amino acid sequence that is at least 40, 50, 60, 70, 80, 90, 95, or 100% identical to the sequence of a region of human merlin or the sequence of full-length human merlin (accession number P35240). In various embodiments, the compound is a purified or unpurified synthetic organic molecule, naturally occurring organic molecule, nucleic acid molecule, PAK kinase antisense nucleic acid or double stranded RNA molecule, biosynthetic protein or peptide, naturally occurring peptide or protein, PAK kinase antibody, or dominant negative PAK kinase protein (e.g., a mutant or fragment of a PAK kinase). In other embodiments, the compound is an autoinhibitory region of a PAK kinase, such as a protein that includes or consists of at least 25, 50, 75, 100, 125, or 150 contiguous amino acids of residues 82-146 of PAK2 or the corresponding region in another PAK kinase (e.g., residues 83-149 of PAK1). In certain embodiments, the protein includes at least 25, 50, 75, 100, 125, 150, 200, or 300 of the N-terminal amino acids of a PAK kinase. In some embodiments, the compound is staurosporine or an ATP analog. In other embodiments, the compound is an anti-merlin antibody. Desirably, the amount of phosphorylated merlin that is bound by the antibody is at least 2, 5, 10, or 15-fold greater that the amount of unphosphorylated merlin that is bound.

The invention also features methods for identifying or selecting compounds that decrease PAK kinase activity or decrease the level of merlin phosphorylation and thus are useful for treating or preventing cancer in a mammal (e.g., a human).

Accordingly, in one aspect, the invention features a screening method for determining whether a compound is useful for treating, stabilizing, or preventing cancer in a mammal. This method involves measuring PAK kinase activity in a cell, tissue, or mammal in the presence and absence of the compound. The compound is determined to treat, stabilize, or prevent cancer if the compound decreases PAK kinase activity. In some embodiments, the method also includes administering the compound to a mammal in need of the treatment (e.g., a mammal with cancer or an increased risk for cancer). In certain embodiments, the compound is a member of a library of at least 5, 10, 15, 20, 30, 50, or more compounds, all of which are simultaneously administered to the cell, tissue, or mammal. In various embodiments, the compound is a purified or unpurified synthetic organic molecule, naturally occurring organic molecule, nucleic acid molecule, PAK kinase antisense nucleic acid or double stranded RNA molecule, biosynthetic protein or peptide, naturally occurring peptide or protein, PAK kinase antibody, or dominant negative PAK kinase protein (e.g., a mutant or fragment of a PAK kinase). In other embodiments, the compound is an autoinhibitory region of a PAK kinase, such as a protein that includes or consists of at least 25, 50, 75, 100, 125, or 150 contiguous amino acids of residues 82-146 of PAK2 or the corresponding region in another PAK kinase (e.g., residues 83-149 of PAK1). In certain embodiments, the protein includes at least 25, 50, 75, 100, 125, 150, 200, or 300 of the N-terminal amino acids of a PAK kinase. In some embodiments, the compound is staurosporine or an ATP analog. In desirable embodiments, the compound decreases an activity of a PAK kinase (e.g., the phosphorylation of merlin), the level of a PAK kinase mRNA or protein, the half-life of a PAK kinase mRNA or protein, the binding of a PAK kinase to a substrate or to another molecule, or the level or activity of a protein that phosphorylates a PAK kinase. Desirably, the level of a PAK kinase mRNA or protein, an activity of a PAK kinase, the half-life of a PAK kinase mRNA or protein, the binding of a PAK kinase to another molecule, or the level or activity of a protein that phosphorylates a PAK kinase decreases by at least 5, 10, 20, 30, 40, 50, 60, or 80, 90, 95, or 100%.

In a related aspect, the invention features another screening method for determining whether a compound is useful for treating, stabilizing, or preventing cancer in a mammal. This method involves measuring the phosphorylation level of merlin (e.g., phosphorylation of serine 518) in a cell, tissue, or mammal in the presence and absence of the compound. The compound is determined to treat, stabilize, or prevent cancer if the compound decreases the phosphorylation level of merlin. In some embodiments, the method also includes administering the compound to a mammal in need of the treatment (e.g., a mammal with cancer or an increased risk for cancer). In certain embodiments, the compound is a member of a library of at least 5, 10, 15, 20, 30, 50, or more compounds, all of which are simultaneously administered to the cell, tissue, or mammal. In various embodiments, the compound is a purified or unpurified synthetic organic molecule, naturally occurring organic molecule, nucleic acid molecule, PAK kinase antisense nucleic acid or double stranded RNA molecule, biosynthetic protein or peptide, naturally occurring peptide or protein, PAK kinase antibody, or dominant negative PAK kinase protein (e.g., a mutant or fragment of a PAK kinase). In other embodiments, the compound is an autoinhibitory region of a PAK kinase, such as a protein that includes or consists of at least 25, 50, 75, 100, 125, or 150 contiguous amino acids of residues 82-146 of PAK2 or the corresponding region in another PAK kinase (e.g., residues 83-149 of PAK1). In certain embodiments, the protein includes at least 25, 50, 75, 100, 125, 150, 200, or 300 of the N-terminal amino acids of a PAK kinase. In some embodiments, the compound is staurosporine or an ATP analog. In other embodiments, the compound is an anti-merlin antibody. Desirably, the amount of phosphorylated merlin that is bound by the antibody is at least 2, 5, 10, or 15-fold greater that the amount of unphosphorylated merlin that is bound. In desirable embodiments, the compound decreases the percentage of merlin that is phosphorylation or the total amount of phosphorylated merlin by at least 5, 10, 20, 30, 40, 50, 60, 80, 90, 95, or 100%. Exemplary merlin proteins have an amino acid sequence that is at least 40, 50, 60, 70, 80, 90, 95, or 100% identical to the sequence of a region of human merlin or the sequence of full-length human merlin (accession number P35240).

The invention also features pharmaceutical compositions for the treatment or prevention of cancer. In one such aspect, the invention features a pharmaceutical composition that includes one or more compounds that inhibit PAK kinase activity and/or merlin phosphorylation in an acceptable vehicle. In some embodiments, the composition contains between 10 ng and 10 mg, such as between 0.1 to 1 mg, of the compound. In various embodiments, the compound is a synthetic organic molecule, naturally occurring organic molecule, nucleic acid molecule, PAK kinase antisense nucleic acid or double stranded RNA molecule, biosynthetic protein or peptide, naturally occurring peptide or protein, PAK kinase antibody (e.g., an antibody that specifically binds a PAK kinase such as PAK2), or dominant negative PAK kinase protein (e.g., a mutant or fragment of a PAK kinase). In other embodiments, the compound is an autoinhibitory region of a PAK kinase, such as a protein that includes or consists of at least 25, 50, 75, 100, 125, or 150 contiguous amino acids of residues 82-146 of PAK2 or the corresponding region in another PAK kinase (e.g., residues 83-149 of PAK1). In certain embodiments, the protein includes at least 25, 50, 75, 100, 125, 150, 200, or 300 of the N-terminal amino acids of a PAK kinase. In some embodiments, the compound is staurosporine or an ATP analog. In other embodiments, the compound is an anti-merlin antibody. Desirably, the amount of phosphorylated merlin that is bound by the antibody is at least 2, 5, 10, or 15-fold greater that the amount of unphosphorylated merlin that is bound. In desirable embodiments, the compound decreases the percentage of merlin that is phosphorylation, the total amount of phosphorylated merlin, or an activity of a PAK kinase by at least 5, 10, 20, 30, 40, 50, 60, 80, 90, 95, or 100%.

Suitable carriers include, but are not limited to, saline, buffered saline, dextrose, water, glycerol, ethanol, and combinations thereof. The composition can be adapted for the mode of administration and can be in the form of, for example, a pill, tablet, capsule, spray, powder, or liquid. In some embodiments, the pharmaceutical composition contains one or more pharmaceutically acceptable additives suitable for the selected route and mode of administration. These compositions may be administered by, without limitation, any parenteral route including intravenous, intra-arterial, intramuscular, subcutaneous, intradermal, intraperitoneal, intrathecal, as well as topically, orally, and by mucosal routes of delivery such as intranasal, inhalation, rectal, vaginal, buccal, and sublingual. In some embodiments, the pharmaceutical compositions of the invention are prepared for administration to vertebrate (e.g., mammalian) subjects in the form of liquids, including sterile, non-pyrogenic liquids for injection, emulsions, powders, aerosols, tablets, capsules, enteric coated tablets, or suppositories.

Exemplary cancers that can be treated, stabilized, or prevented using the above methods include cancers of the nervous system (e.g., Schwann cell tumors or Nf2), prostate cancers, breast cancers, ovarian cancers, pancreatic cancers, gastric cancers, bladder cancers, salivary gland carcinomas, gastrointestinal cancers, lung cancers, colon cancers, melanomas, brain tumors, leukemias, lymphomas, and carcinomas. Benign tumors may also be treated or prevented using the methods and compounds of the present invention. Exemplary mammals include humans, primates such as monkeys, animals of veterinary interest (e.g., cows, sheep, goats, buffalos, and horses), and domestic pets (e.g., dogs and cats).

With respect to the therapeutic methods of the invention, it is not intended that the administration of compounds to a mammal be limited to a particular mode of administration, dosage, or frequency of dosing; the present invention contemplates all modes of administration, including oral, intraperitoneal, intramuscular, intravenous, intraarticular, intralesional, subcutaneous, or any other route sufficient to provide a dose adequate to prevent or treat cancer. One or more compounds may be administered to the mammal in a single dose or multiple doses. When multiple doses are administered, the doses may be separated from one another by, for example, one week, one month, one year, or ten years. It is to be understood that, for any particular subject, specific dosage regimes should be adjusted over time according to the individual need and the professional judgment of the person administering or supervising the administration of the compositions. If desired, conventional treatments such as radiation therapy, chemotherapy, and/or surgery may be used in combination with the compounds of the present invention.

In various embodiments of any of the aspects of the invention, the compound has a molecular weight contained in one of the following ranges: 100-4,000 daltons, 100-3,000 daltons; 100-2,000 daltons; 100-1,000 daltons; 100-750 daltons; 250-4,000 daltons, 250-3,000 daltons; 250-2,000 daltons; 250-1,000 daltons; 250-750 daltons; 400-4,000 daltons, 400-3,000 daltons; 400-2,000 daltons; 400-1,000 daltons; or 400-750 daltons, inclusive.

By "AK kinase" is meant a protein with an amino acid sequence that is at least 40, 50, 60, 70, 80, 90, 95, or 100% identical to the sequence of a region (e.g., a region of at least 50, 100, 150, or 200 amino acids) of a p21-activted kinase (PAK) or the sequence of a full-length PAK. Exemplary PAK kinases have a sequence at least 40, 50, 60, 70, 80, 90, 95, or 100% identical to human PAK1, 2, 3, 4, 5, or 6 over its entire sequence. Examples of human PAK kinase sequences are deposited under the following accession numbers: Q13153 (PAK1), Q13177 (PAK2), O75914 (PAK3), NP_005875 (PAK4), BAA94194 (PAK5), and NP_064553 (PAK6). Desirably, the level of an activity of the PAK kinase (e.g., phosphorylation of merlin) is at least 30, 50, 60, 70, 80, 90, 95, or 100% of the level of the corresponding activity of human PAK1, 2, 3, 4, 5, or 6. PAK kinases belong to a larger group of the STE20-like kinases.

By "compound that decreases PAK kinase activity" is meant a compound that decreases the level of a PAK kinase mRNA or protein, an activity of a PAK kinase, the half-life of a PAK kinase mRNA or protein, or the binding of a PAK kinase to another molecule (e.g., a substrate for a PAK kinase, a Rac protein, or a cdc42 protein), as measured using standard methods (see, for example, Ausubel et al., Current Protocols in Molecular Biology, Chapter 9, John Wiley & Sons, New York, 2000). For example, the compound may directly or indirectly inhibit the ability of a PAK kinase to phosphorylate merlin. In other desirable embodiments, a compound that decreases PAK kinase activity reduces or stabilizes the level of Rac or cdc42 mRNA or protein and thus reduces or stabilizes the level of an activated PAK kinase. mRNA expression levels may be determined using standard RNase protection assays or in situ hybridization assays, and the level of protein may be determined using standard Western or immunohistochemistry analysis (see, for example, Ausubel et al., supra). The phosphorylation levels of signal transduction proteins downstream of merlin acitivity may also be measured using standard assays. Desirably, the compound decreases PAK kinase activity by at least 20, 40, 60, 80, or 90%. In another desirable embodiment, the level of PAK kinase activity is at least 2, 3, 5, 10, 20, or 50-fold lower in the presence of the compound. In yet another desirable embodiment, the compound preferentially decreases the expression or kinase activity of PAK2; for example, the compound may decrease the expression or kinase activity of PAK2 by at least 50, 100, 200 or 500% more than it decreases the expression or kinase activity of another PAK kinase, such as PAK1, PAK3, PAK4, PAK5, or PAK6. Other desirable compounds decrease the expression or kinase activity of multiple PAK kinases (e.g., 2, 3, 4, 5, 6, or more PAK kinases). Desirably, the level of PAK2 mRNA, PAK2 protein, or PAK2 kinase activity in the presence of the compound is less than 80, 60, 40, or 20% of the corresponding level in the absence of the compound. Desirably, the decrease in PAK kinase activity in the central nervous system is at least 2, 3, 5, 10, 20, or 50-fold greater than the decrease in PAK kinase activity in the periphery or than the decrease in the activity of another kinase. It is also contemplated that the expression or activity of a protein having an amino acid sequence that is substantially identical to that of a PAK kinase may be inhibited.

Compounds that may be tested for their ability to decrease PAK kinase activity include, but are not limited to, synthetic organic molecules, naturally occurring organic molecules, nucleic acid molecules, PAK kinase antisense nucleic acids or double stranded RNA molecules, biosynthetic proteins or peptides, naturally occurring peptides or proteins, PAK kinase antibodies, or dominant negative PAK kinase proteins. Because sequences within PAK kinases are autoinhibitory, peptides or peptide analogs based on these autoinhibitory regions may be used as inhibitors of PAK kinase activity (Maruta et al., Ann. N.Y. Acad. Sci., 886:48-57, 1999). Additionally, the autoinhibitory domain of PAK2 that is described herein may be used as an inhibitor of PAK kinase activity or may be used as an initial structure for the design of other peptides or peptide analogs that inhibit PAK kinase activity. Other exemplary PAK kinase inhibitors include staurosporine, staurosporine analogs, and pharmacuetically acceptable salts thereof (Zeng et al., J. Cell Sci. 113 (Pt 3): 471-82, 2000; Yu et al., J Biochem (Tokyo), 129(2): 243-51, 2001). Exemplary PAK kinase inhibitors which may inhibit PAK kinases indirectly include those reported by He et al. (Cancer J. 7(3): 191-202, 2001, Cancer J. 6(4):243-8, 2000). Still other preferred compounds include ATP analogs.

By "antibody that specifically binds a protein" is meant an antibody that binds to a PAK kinase or merlin, but does not substantially bind to other molecules in a sample, e.g., a biological sample, that naturally includes a PAK kinase or merlin. Desirably, the amount antibody bound to a PAK kinase or merlin is at least 50%, 100%, 200%, 500%, or 1,000% greater than the amount of antibody bound to other proteins under the same conditions. In some embodiments, the amount of antibody bound to PAK2 is at least 2, 5, 10, or 20-fold more than the amount bound to another PAK kinase, such as PAK1, PAK3, PAK4, PAK5, or PAK6. Desirably, the antibody decreases the activity of a PAK kinase and/or the phosphorylation level of merlin by at least 30, 50, 60, 70, 80, 90, 95, or 100%. In various embodiments, the antibody is a modified antibody, bifunctional antibody, or antibody fragment.

By "modified antibody" is meant an antibody having an altered amino acid sequence so that fewer antibodies and/or immune responses are elicited against the modified antibody when it is administered to a mammal such as a human. For example, the constant region of the antibody may be replaced with the constant region from a human antibody. For the use of the antibody in a mammal other than a human, an antibody may be converted to that species format.

By "bifunctional antibody" is meant an antibody that includes an antibody or a fragment of an antibody covalently linked to a different antibody or a different fragment of an antibody. In one preferred embodiment, both antibodies or fragments bind to different epitopes expressed on a PAK kinase. Other preferred bifunctional antibodies bind to two different antigens, such as to two different PAK kinases. Standard molecular biology techniques such as those described herein may be used to operably link two nucleic acids so that the fusion nucleic acid encodes a bifunctional antibody.

By "fragment" is meant a polypeptide having a region of consecutive amino acids that is identical to the corresponding region of an antibody of the invention but is less than the full-length sequence. The fragment has the ability to bind the same antigen as the corresponding antibody based on standard assays, such as those described herein. Desirably, the binding of the fragment to a PAK kinase is at least 20, 40, 60, 80, or 90% of that of the corresponding antibody.

By "antisense" is meant a nucleic acid, regardless of length, that is complementary to the coding strand or mRNA of a PAK kinase. In some embodiments, the antisene molecule inhibits the expression of only one PAK kinase, and in other embodiments, the antisense molecule inhibits the expression of more than one PAK kinase. Desirably, the antisense nucleic acid decreases the expression or biological activity of a PAK kinase by at least 20, 40, 50, 60, 70, 80, 90, 95, or 100%. A antisense molecule can be introduced, e.g., to an individual cell or to whole animals, for example, it may be introduced systemically via the bloodstream.

In some embodiments, the antisense molecule is less than 200, 150, 100, 75, 50, or 25 nucleotides in length. In other embodiments, the antisense molecule is less than 50,000; 10,000; 5,000; or 2,000 nucleotides in length. In certain embodiments, the antisense molecule is at least 200, 300, 500, 1000, or 5000 nucleotides in length. In some embodiments, the number of nucleotides in the antisense molecule is contained in one of the following ranges: 5-15 nucleotides, 16-20 nucleotides, 21-25 nucleotides, 26-35 nucleotides, 36-45 nucleotides, 46-60 nucleotides, 61-80 nucleotides, 81-100 nucleotides, 101-150 nucleotides, or 151-200 nucleotides, inclusive. In addition, the antisense molecule may contain a sequence that is less than a full length sequence or may contain a full-length sequence.

By "double stranded RNA" is meant a nucleic acid containing a region of two or more nucleotides that are in a double stranded conformation. In various embodiments, the double stranded RNA consists entirely of ribonucleotides or consists of a mixture of ribonucleotides and deoxynucleotides. The double stranded RNA may be a single molecule with a region of self-complimentarity such that nucleotides in one segment of the molecule base pair with nucleotides in another segment of the molecule. Alternatively, the double stranded RNA may include two different strands that have a region of complimentarity to each other. Desirably, the regions of complimentarity are at least 70, 80, 90, 95, 98, or 100% complimentary. Desirably, the region of the double stranded RNA that is present in a double stranded conformation includes at least 5, 10, 20, 30, 50, 75, 100, 200, 500, 1000, 2000 or 5000 nucleotides or includes all of the nucleotides in the double stranded RNA. Desirable double stranded RNA molecules have a strand or region that is at least 70, 80, 90, 95, 98, or 100% identical to a coding region or a regulatory sequence (e.g., a transcription factor binding site, a promoter, or a 5' or 3' untranslated region) of a PAK kinase. In some embodiments, the double stranded RNA is less than 200, 150, 100, 75, 50, or 25 nucleotides in length. In other embodiments, the double stranded RNA is less than 50,000; 10,000; 5,000; or 2,000 nucleotides in length. In certain embodiments, the double stranded RNA is at least 200, 300, 500, 1000, or 5000 nucleotides in length. In some embodiments, the number of nucleotides in the double stranded RNA is contained in one of the following ranges: 5-15 nucleotides, 16-20 nucleotides, 21-25 nucleotides, 26-35 nucleotides, 36-45 nucleotides, 46-60 nucleotides, 61-80 nucleotides, 81-100 nucleotides, 101-150 nucleotides, or 151-200 nucleotides, inclusive. In addition, the double stranded RNA may contain a sequence that is less than a full-length sequence or may contain a full-length sequence.

In some embodiments, the double stranded RNA molecule inhibits the expression of only one PAK kinase, and in other embodiments, the double stranded RNA molecule inhibits the expression of more than one PAK kinase. Desirably, the nucleic acid decreases the expression or biological activity of a PAK kinase by at least 20, 40, 50, 60, 70, 80, 90, 95, or 100%. A double stranded RNA can be introduced, e.g., to an individual cell or to whole animals, for example, it may be introduced systemically via the bloodstream.

In various embodiments, the double stranded RNA or antisense molecule includes one or more modified nucleotides in which the 2' position in the sugar contains a halogen (such as flourine group) or contains an alkoxy group (such as a methoxy group) which increases the half-life of the double stranded RNA or antisense molecule in vitro or in vivo compared to the corresponding double stranded RNA or antisense molecule in which the corresponding 2' position contains a hydrogen or an hydroxyl group. In yet other embodiments, the double stranded RNA or antisense molecule includes one or more linkages between adjacent nucleotides other than a naturally-occurring phosphodiester linkage. Examples of such linkages include phosphoramide, phosphorothioate, and phosphorodithioate linkages.

By "purified" is meant separated from other components that naturally accompany it. Typically, a factor is substantially pure when it is at least 50%, by weight, free from proteins, antibodies, and naturally-occurring organic molecules with which it is naturally associated. Desirably, the factor is at least 75%, more desirably, at least 90%, and most desirably, at least 99%, by weight, pure. A substantially pure factor may be obtained by chemical synthesis, separation of the factor from natural sources, or production of the factor in a recombinant host cell that does not naturally produce the factor. Proteins, vesicles, organelles, and small molecules may be purified by one skilled in the art using standard techniques such as those described by Ausubel et al. (Current Protocols in Molecular Biology, John Wiley & Sons, New York, 2000). The factor is desirably at least 2, 5, or 10 times as pure as the starting material, as measured using polyacrylamide gel electrophoresis, column chromatography, optical density, HPLC analysis, or western analysis (Ausubel et al., supra). Preferred methods of purification include immunoprecipitation, column chromatography such as immunoaffinity chromatography, magnetic bead immunoaffinity purification, and panning with a plate-bound antibody.

By "treating, stabilizing, or preventing cancer" is meant causing a reduction in the size of a tumor, slowing or preventing an increase in the size of a tumor, increasing the disease-free survival time between the disappearance of a tumor and its reappearance, preventing an initial or subsequent occurrence of a tumor, or reducing an adverse symptom associated with a tumor. In one desirable embodiment, the number of cancerous cells surviving the treatment is at least 20, 40, 60, 80, or 100% lower than the initial number of cancerous cells, as measured using any standard assay. Desirably, the decrease in the number of cancerous cells induced by administration of a compound of the invention is at least 2, 5, 10, 20, or 50-fold greater than the decrease in the number of non-cancerous cells. In yet another desirable embodiment, the number of cancerous cells present after administration of an compound that inhibits PAK kinase activity or inhibits merlin phosphorylation is at least 2, 5, 10, 20, or 50-fold lower than the number of cancerous cells present prior to the administration of the compound or after administration of a buffer control. Desirably, the methods of the present invention result in a decrease of 20, 40, 60, 80, or 100% in the size of a tumor as determined using standard methods. Desirably, at least 20, 40, 60, 80, 90, or 95% of the treated subjects have a complete remission in which all evidence of the cancer disappears. Desirably, the cancer does not reappear or reappears after at least 5, 10, 15, or 20 years. Examples of cancers that may be treated using these methods include familial and sporadic tumors of the nervous system, such as schwannomas, meningiomas, or ependymomas.

By "mutation" is meant an alteration in a naturally-occurring or reference nucleic acid sequence, such as an insertion, deletion, frameshift mutation, silent mutation, nonsense mutation, or missense mutation. Desirably, the amino acid sequence encoded by the nucleic acid sequence has at least one amino acid alteration from a naturally-occurring sequence.

By "substantially identical" is meant having a sequence that is at least 60, 70, 80, 90, 95, or 100% identical to that of another sequence. Sequence identity is typically measured using sequence analysis software with the default parameters specified therein (e.g., Sequence Analysis Software Package of the Genetics Computer Group, University of Wisconsin Biotechnology Center, 1710 University Avenue, Madison, Wis. 53705). This software program matches similar sequences by assigning degrees of homology to various substitutions, deletions, and other modifications.

BRIEF DESCRIPTION OF THE DRAWINGS

FIG. 5A is a picture of the Western blot analysis of increasing amounts of merlin precipitated from LLC-PK1 extracts. FIG. 5B is a picture of the Western blot analysis of wild-type and S518A merlin in LLC-PK1 transfected cells. FIG. 5C is a picture illustrating the immunolocalization of merlin with SC331 and HM2175. Wild type merlin (panel 1), merlin S518A (panel 2), merlin S518D (panel 3), merlin+active PAK2 (panel 4), staining with HM2175 of wild type merlin (panel 5) and merlin S518A (panel 6).

DETAILED DESCRIPTION

Figure 1A:
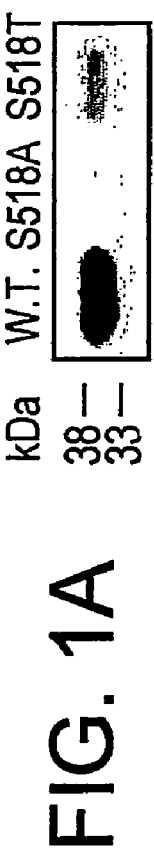
FIGS. 1A-1C illustrate the result of a kinase assay with merlin-substrate and full-length merlin. In vitro kinase assay was performed with the GST-merlin fragment pseudo-substrate (FIGS. 1A and 1B) or with full-length merlin (FIG. 1C). Substrates were precipitated and resolved by SDS-PAGE and exposed to film. "W.T." denotes wild-type; "S518A" denotes alanine mutant; "S518T" denotes threonine mutant; "Ind" denotes serum induced extract, and "606 N.I." denotes non induced.

We discovered that the phosphorylation of the tumor suppressor merlin at serine 518 is induced by the p21-activated kinase PAK2. This phosphorylation of merlin was demonstrated by biochemical fractionation, use of active and dominant-negative mutants of PAK2, effector activation defective mutants of Rac/cdc42, immunodepletion, and co-immunoprecipitation. Wild-type and mutated forms of merlin and phospho-specific antibodies were used to show that phosphomerlin is enhanced in membrane protrusions in epithlial cells.

The data regarding merlin phosphorylation indicate that phosphorylation of merlin "inactivates" merlin's function by opening the protein and disrupting merlin intra- and intermolecular associations. Thus, phosphorylation of merlin by PAK may be equated to inactivation of merlin by disease causing mutations. In light of this information, and the fact that a large number of the above-mentioned tumor types of the central nervous system do not present with mutations in the Nf2 locus, we believe that the required inactivation of merlin in the tumors is achieved by up-regulation of merlin phosphorylation by p21-activated kinases. Hence, administration of a specific p21-activated kinase inhibitor may down regulate merlin phosphorylation and restore merlin function as a tumor suppressor.

Thus, a variety of cancers (e.g., cancers of the central nervous system) can be prevented or treated by administering one or more compounds that inhibit PAK kinase activity and/or phosphorylation of merlin. Compounds useful in these methods can be identified in standard assays such as those described herein. These therapeutic and screening methods are described further below.

Methods for Analysis of PAK Kinase Activity and Merlin Phosphorylation Plasmids and Transfections Wild-type merlin and S518A were subcloned from previously described vectors (Shaw et al., supra) into the BamH1-EcoRI sites of pcDNA3 (Invitrogen). The merlin GST-substrates were prepared by PCR amplification of the 60 amino acid coding sequences from the wild-type and S518A versions of merlin. The primers used were: 5'-CCAGGAATTC-CATTGCCACCAAGCCCACGTACCCG-3' (SEQ ID NO:1) and 5'-GCAAGCATCTGCAGGAGCACCTCGACTC-GAGCGGCC-3' (SEQ ID NO:2). The fragments were then cut with EcoRI and XhoI and ligated into pGEX5-3x. Pak2 wild-type and active forms: wild-type PAK2 was amplified and cloned into the BamHI and XhoI sites of pcDNA3 (Invitrogen). The T402E mutation was created by site-directed mutagenesis using the Quick-change kit, as instructed by the manufacturer (Stratgene). The primers used were: 5'-GCA-GAGCAAACGCAGTGAGATGGTCGGAACGCC-3' (SEQ ID NO:3) and 5'-GGCGTTCCGACCATCTCACT-GCGTTTGCTCTGC-3' (SEQ ID NO:4). The PAK2 auto inhibitory domain was amplified using 5'-CCGCTCGAGAT-GCACACCATCCATGTTGGC-3' (SEQ ID NO:5) and 5'-GCTCTAGATTAATCTTTCTCAGGAGGAGTAAAGC-3' (SEQ ID NO:6) and cloned into the XhoI and XbaI sites of pcDNA3. All plasmids were transfected in to the various cell lines using Lipofectamine (Life Technologies) according to manufacturer's instructions.

In-Vitro Kinase Assay

Total cellular extracts were prepared by lysing the cells directly in cell lysis buffer; 50 mm HEPES pH=7.4, 1% NP-40, 150 mM NaCl, 25 mM NaF, 20 mM β-glycerophosphate, 1 mM EDTA, and protease inhibitors. The extracts were added into reaction tubes containing 200 ng GST-substrate, 2 mM MgCl, 2 mM DTT, 100M cold ATP and 10 μCi $p^{32}$ [γ]-ATP. For the immunodepeletion experiments extracts were incubated with the relevant antibody for three hours at 4° C. After four sequential exchanges of antibody, the presence of the protein in question was determined by western blot analysis. Kinase reactions were carried out at 30° C. for 20 minutes. The substrate was washed three times in lysis buffer at 4° C. Termination of the reaction was by addition of protein sample buffer and boiling for five minutes. The samples were then resolved by SDS-PAGE, dried on 3 MM paper (Whatman), and exposed to X-ray film.

Merlin Phosphorylation

In the in-vitro kinase assays where full-length merlin was used, cells transfected with merlin expression vectors were extracted, and merlin was immunoprecipitated using a commercially available antibody SC-331 (Santa Cruz) and Protein A-agarose beads. In the in-vivo studies, cells were transfected with various expression vectors and harvested after 48 hours into SDS-boiling buffer (10 mM Tris pH 7.5, 50 mM NaF, and 1% SDS). Cells were scraped off the plates and boiled for 5'. Protein concentration was determined by the BCA method (Pierce) and resolved by 9% SDS-PAGE and western blot analysis.

Kinetics of Merlin Phlosphorylation and PAK Activation

In the time course study of merlin phosphorylation, NIH3T3 cells were transfected with either merlin or PAK2 expression vectors. Fourty-eight hours post transfection, the cells were serum starved for 24 hours and then trypsinized, washed, and transferred to poly-HEME coated plates for three hours. Cells were then plated unto coated tissue culture dishes for various periods of time and collected into SDS-boiling buffer. The protein was concentration was determined, and the protein was resolved on 9% SDS-PAGE and western blot analysis. For activation of PAK2, the extracts were immunoprecipitated with a commercially available antibody (Zymed) and resolved in an in-gel kinase assay using histone H4, as previously described (Price et al., Mol. Biol. Cell 9:1863-1871, 1998).

Production of Phospho-Specific Antibodies and Commercial Antibodies

A chemically phosphorylated peptide: [H}-CKDTDMKRLS*MEIE—[NH2] (SEQ ID NO: 7 was coupled to SulfoLink coupling gel (Pierce) and used to immunize rabbits. A standard protocol of immunization was employed. Sera from the animals were then purified in two steps. First the sera was passed over an affinity column of the phospho-antigen. This column binds antibodies recognizing the phosphorylated and/or unphosphorylated forms of the peptide. In a second step, the bound fraction of the first column was applied to a second column of the unphosphorylated peptide. The flow-through was collected and contained only phospho-specific antibodies.

Biochemical Fractionation of Merlin-Kinase Activity

Ion-exchange chromatography was performing using a Q-sepharose (Pharmacia) 10_10 column at pH=8.5 (Diethanolamine buffer) to which a linear NaCl gradient was applied. Maximal activity eluted around 120-130 mM NaCl. A 60-fold enrichment was achieved with overall recovery of about 70%. For dye-ligand chromatography, a Matrex Red A dye (Millipore) 10_10 column was used (pH 8, 0-500 mM KCl linear gradient), yielding a 10-fold enrichment with 25% recovery. For gel filtration, best results were achieved with a 10_30 superose 6 column (Pharmacia) at a flow rate of 0.2 ml/min.

Immunoflouresence

NIH3T3 or LLC-PK1 cells were plated on glass cover slips and transfected with various expression vectors. Twenty-four hours post transfection cells were fixed in 4% paraformaldhyde for 15' and permabilized with Triton X-100 for 10'. Sc-331 was used at 1:1000 dilution and HM2175 was used at 1.0 μg/ml.

Merlin Pseudo-Substrate is Phosphorylated In-Vitro by PAK2

Figure 1B:
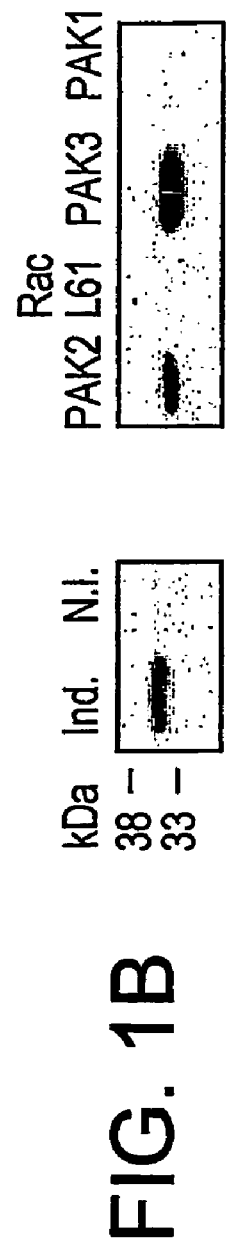
Figure 1C:
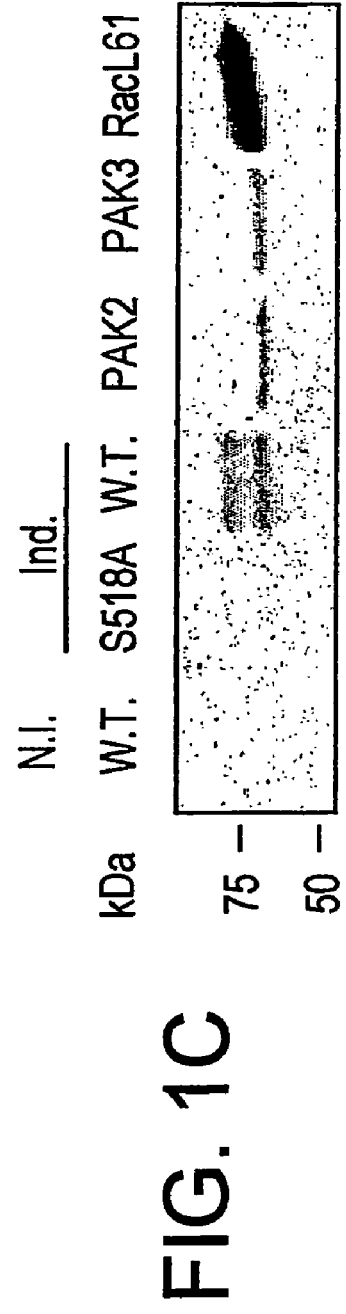

Merlin is phosphorylated in response to various stimuli such as serum starvation, confluency and detachment. To identify the kinase that phosphorylates merlin on serine 518, an in-vitro kinase assay was established. The assay employs a pseudo-substrate comprised of residues 478-535 of merlin fused to glutathione-S-transferase (GST). The pseudo-substrate was produced in bacteria and then used in an in-vitro kinase assay bound to gluthathione-agarose beads. Kinase activity was determined using SDS-PAGE and autoradiography. The specificity of this assay was demonstrated by the inability of a substrate in which serine 518 was mutated to alanine 518 (S518A) to be phosphorylated to any significant extent under the conditions tested (FIG. 1A). The phosphorylation of the pseudo-substrate was then examined using extracts from cells grown under conditions that induce merlin phosphorylation in vivo. For example, serum shock and reattachment induce strong phosphorylation of merlin in vivo and of the pseudo-substrate in vitro (FIG. 1B left). When the pseudo-substrate was substituted with full-length wild-type merlin and merlin S518A in the same in vitro kinase assay, a similar pattern of phosphorylation was observed (FIG. 1C).

Once validated, the kinase assay was then employed in a candidate-based screen for merlin-kinase. In these screens, NIH3T3 cells were transfected with the expression vectors for various Rac/cdc42 activated kinases, and the protein extracts were then employed in the kinase assay with ATP-γ-$P^{32}$. After several washes, the substrate was resolved by SDS-PAGE and exposed to film. Only extracts from cells transfected with PAK2 and PAK3 were able to effectively phosphorylate the pseudo-substrate in an in-vitro kinase assay (FIG. 1B). Other kinases, which are known effectors of cdc42/Rac, including PAK1, LIM-kinase and JNK, did not induce phosphorylation of merlin in these assays. Similar results were observed when the in-vitro kinase assays were preformed with immunoprecipitated full-length merlin. In this case, the levels of phosphorylating activity from extracts prepared with RacL61 were significantly higher than with the PAK2/PAK3 extracts (FIG. 1C).

PAK2 Levels Correlate with Enrichment for the Merlin Kinase Activity

Figure 2A:
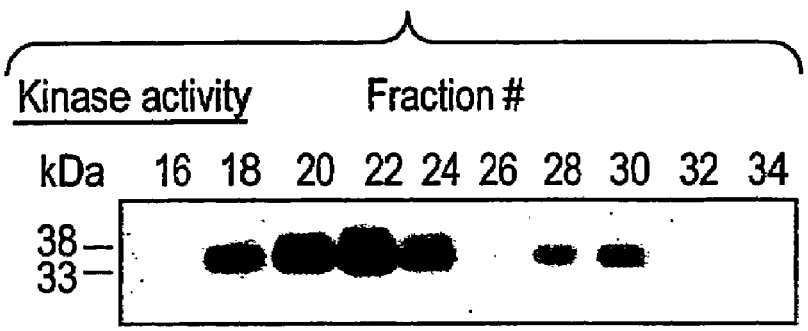
FIGS. 2A and 2B illustrate the chromatographic separation of merlin kinase activity. Merlin kinase activity was separated on a Q-sepharose 10_10 column. Fractions were monitored for activity by in-vitro kinase assay with the pseudo-substrate and Western blot analysis for PAK3 (FIG. 2A). In a subsequent step, fractions 13-15 were further resolved on a Matrex Red dye-ligand column. Kinase activity and PAK2 were followed (FIG. 2B). "L" denotes the load fraction.
Figure 2A:
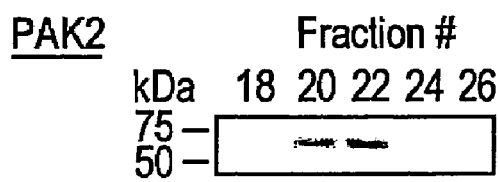
Figure 2A:
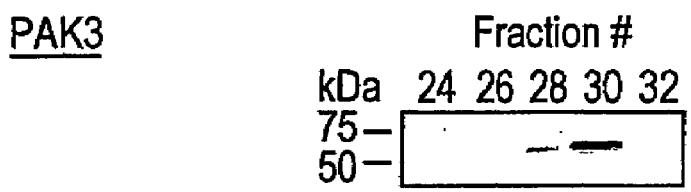
Figure 2B:
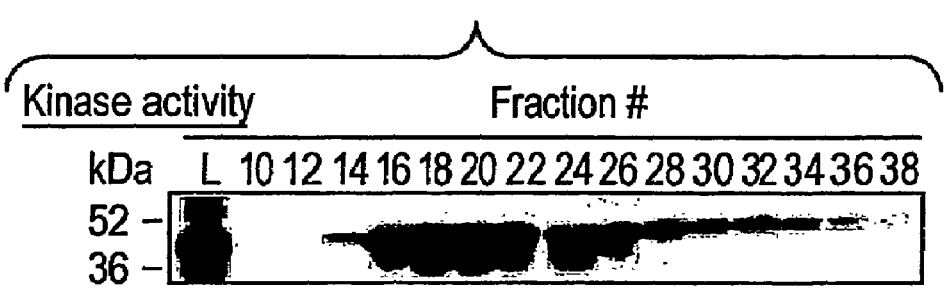
Figure 2B:
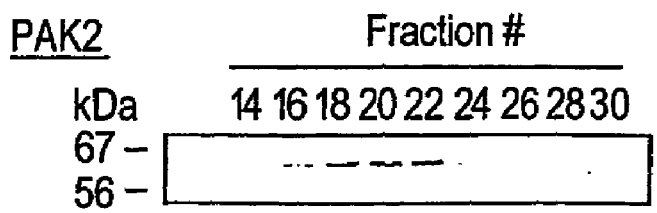

To discriminate between PAK2 and PAK3 as candidate merlin kinases, the kinase activity was purified over a series of chromatographic steps. Fractions were examined for merlin kinase activity using the in vitro kinase assay and for PAK2 and PAK3 levels by western blotting. After an initial step of ammonium sulfate precipitation, the precipitate containing the activity was separated by ion-exchange chromatography on a Q-sepharose column. As shown in FIG. 2A, the maximal activity of merlin kinase was found in fractions 20-22 in this separation. PAK2 levels also peaked in fractions 20-22, while PAK3 levels peaked around fraction 30. Fractions 20-22 were used in a subsequent step of dye-ligand chromatography. Maximal activity of merlin kinase was observed in fractions 18-22. While PAK2 was present in a pattern the fully overlaps with the peak of merlin kinase activity (FIG. 2B), PAK3 was no longer evident in these fractions. After four steps of enrichment, which included ammonium sulfate precipitation, ion-exchange, dye-ligand chromatography, and gel filtration, a more than 1200-fold enrichment of the kinase activity was achieved. When assessing the fractions of the various chromatographic steps by western blot analysis, PAK2 levels consistently paralleled merlin kinase activity (FIG. 2A).

PAK2 Phosphorylates Merlin In-Vivo

Figure 3A:
FIGS. 3A-3C illustrate the in-vivo analysis of merlin phosphorylation by PAK2. NIH3T3 cells were transfected with various expression vectors and were analyzed by western blot 48 hours post transfection. Extracts prepared from cells transfected with wild type merlin or merlin SS518A with expression vector for active PAK2 (PAK2-$^{T402E}$) (FIG. 3A). Extracts prepared from cells transfected with Active Rae (Rae L61) or active cdc42 (cdc42 V12), full length merlin, and the PAK2 autoinhibitory domain (AID) (FIG. 3B). Extracts from cells transfected with various mutants of Rac or cdc42 and wild-type merlin (FIG. 3C).

To determine whether PAK2 can induce phosphorylation of merlin in vivo, NIH3T3 cells were transfected with expression vectors for one of two different forms of constitutively active-PAK2 and merlin. $PAK2^{T402E}$, an activated mutant similar to $PAK1^{T423E}$ (Manser et al., Mol. Cell Biol. 17:1129-1143, 1997) and $PAK2^{\Delta 1-212}$, an N-terminal truncated form similar to the caspase-activated PAK2 were used for this analysis (Rudel et al., J. Immunol. 160:7-11, 1998). Extracts were made 48 hours post transfection and analyzed by western blot analysis. As shown in FIG. 3A, $PAK2^{T402E}$ caused an increase in the slower migrating, hyperphosphorylated form of merlin. In contrast, the mobility of the merlin S518A mutant was not altered in the presence of $PAK2^{T402E}$. Similar results were observed with $PAK2^{\Delta 1-212}$. Thus, active PAK2 induces phosphorylation of merlin in vivo.

Figure 3B:

The PAK Auto-Inhibitory Domain Inhibition of the Rac-Dependent Phosphorylation of Merlin The N-terminal regulatory domain of the PAKs has been shown to contain an auto-inhibitory domain (AID) (Zhao et al., Mol. Cell Biol. 18:2153-2163, 1998). The inhibitory fragment in PAK2 resides between residues 82-146 (equivalent to the 83-149 AID of PAK1). Previous studies have demonstrated that this domain inhibits PAK activity in trans. To further investigate the role of PAK2 in induction of merlin phosphorylation, the ability of the AID to inhibit this activity was assessed. NIH3T3 cells were co-transfected with expression vectors for merlin, activated Rac, or cdc42 and the PAK2 AID. As shown in FIG. 3B, the inclusion of the PAK2 AID significantly reduced the phosphorylation of merlin. This result is demonstrated by the 3-4-fold decrease in the ratio of hyper-phosphorylated to hypo-phosphorylated merlin in cells in which the transfection included the AID. This result indicates that merlin-kinase activity induced by Rac/cdc42 is sensitive to PAK inhibition.

Impaired Phosphorylation of Merlin by Effector-Activation Defective Mutants of Rac/cdc42

Merlin is regulated at least in part by phosphorylation, which is induced by Rac/cdc42 proteins but not by activated Rho. The Rac and cdc42 proteins belong to the family of the Rho G-proteins. These proteins act as molecular switches, cycling between GTP-bound (ON) and GDP-bound (OFF) states. The G-proteins have intrinsic GTPase activity which hydrolyzes GTP to GDP. Although they are implicated in the regulation of many signaling pathways, they are mostly associated with regulation of cytoskeleton reorganization, gene expression, and membrane trafficking processes such as endocytosis.

Figure 3C:
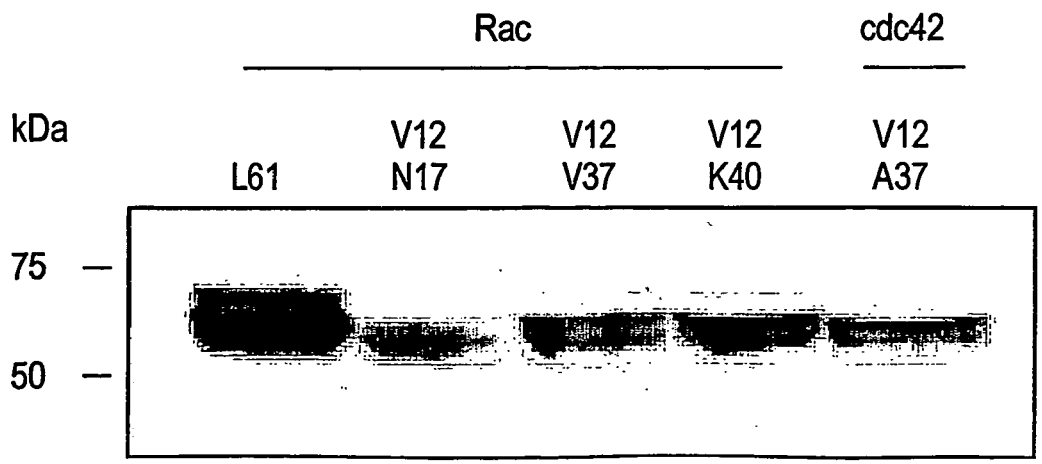

Mutated forms of activated Rac and cdc42 were tested to determine if they maintained the ability to induce the phosphorylation of serine 518. The mutants employed were RacV12V37 and cdc42V12A37, which can activate PAKs but are defective in activation of POR1 and ROKa and induction of cytoskeletal changes, and RacV12K40, which is defective in the activation of PAKs and JNK but able to activate POR and ROKa and induce cytoskeletal changes (Lamarche et al., Cell 87:519-529, 1996; Joneson et al., Science 274:1374-1376, 1996; and Westwick et al., Mol. Cell Biol. 17:1324-1335, 1997). NIH3T3 cells were co-transfected with wild-type merlin and cdc42V12A37, RacV12V37, or RacV12K40. As shown in FIG. 3C, none of the effector domain mutants induced the phosphorylation of merlin to a significant level. These data are consistent with the possibility that more than one Rac-induced effector is required to induce full phosphorylation of merlin. In assays using full-length merlin, RacL61 or cdc42V12 always caused a higher degree of phosphorylation than active forms of PAK2, further suggesting that additional Rac/cdc42-initiated events are involved in this process.

Figure 4A:
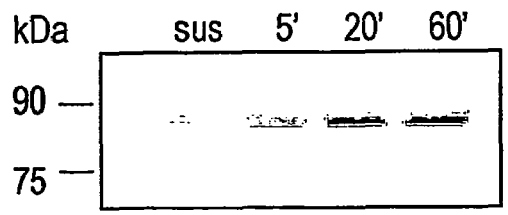
FIGS. 4A-4C show the kinetics of merlin phosphorylation and PAK activation. Western blot analysis of merlin phosphorylation in NIH3T3 cells grown in suspension (sus) and 5', 20', and 60' after re-plating on tissue culture plates (FIG. 4A). Typical profile of PAK activation as measured by fold phosphorylation of histone H4. Activity was assayed at 5', 10', 20', and 60' after re-plating and compared to cells grown in suspension 0' (FIG. 4B). NIH3T3 extracts were immunodepleted with PAK2 or PAK3 antibodies and analyzed by western blot. The merlin-kinase activity in the treated extracts was determined by an in-vitro kinase assay with the merlin substrate and resolved by SDS-PAGE and exposed to film (FIG. 4C).

Similar Kinetics for the Activation of PAK and Merlin Phosphorylation Upon Re-Attachment of Cell to Substratum Merlin phosphorylation is reduced when cells are grown in suspension and induced once the cells are re-plated and begin adhering to the substratum (Shaw et al., J. Biol. Chem. 273: 7757-7764, 1998). Similarly, PAK activity was shown to be increased upon cell attachment (del Pozo et al., Embo 19:2008-2014, 2000). To assess the kinetics of merlin phosphorylation and PAK2 activation in the present system, NIH3T3 cells were co-transfected with wild-type PAK2 or merlin, resuspended, and then allowed to attach to culture plates. Merlin was predominantly in an unphosphorylated state when cells were in suspension (FIG. 4A). However, upon attachment, a steady increase in overall levels of merlin was detected up to 20 minutes after plating, then the levels plateaued. In addition, a 2-3 fold increase in the levels of the phosphorylated form of merlin was observed five minutes after plating. This level of phosphorylation remained constant up to one hour after re-plating.

Figure 4B:
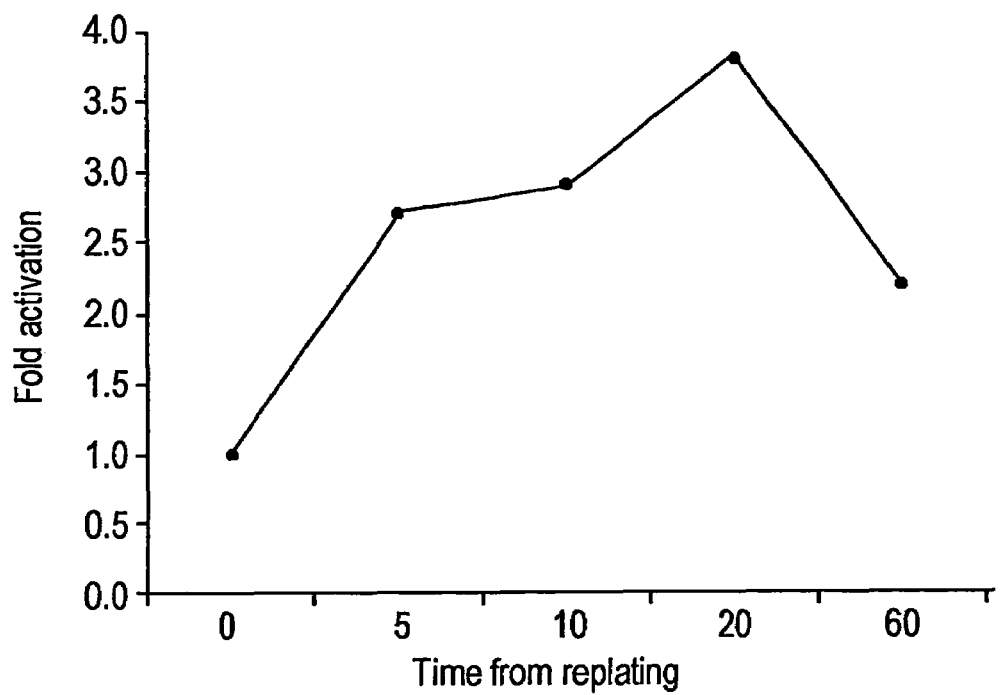

The kinase activity of PAK2 was determined over this time course using immunoprecipitated protein and histone H4 as a substrate. As shown in FIG. 4B, PAK2 kinase activity was increased approximately 3-fold at five minutes post-attachment. Maximal activity was observed at 20 minutes, and at one hour the activity was reduced again. Thus, the phosphorylation of merlin five minutes after replating correlates well with activation of PAK2 kinase activity. The addition of serum to the cells in suspension does not induce activation of PAK2 or the phosphorylation of merlin. This result is in agreement with previous reports and demonstrates the requirement of cell adhesion for both processes.

Reduced Merlin-Kinase Activity Following Immunodepletion of PAK2

Figure 4C:
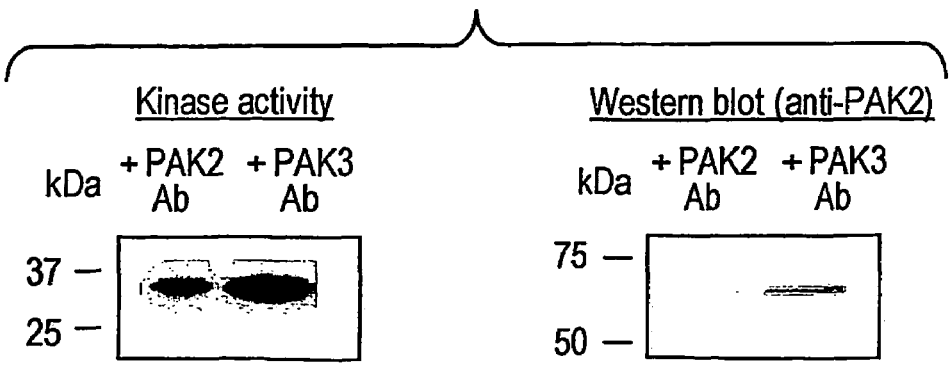

To investigate further whether PAK2 is directly responsible for merlin phosphorylation, the enzyme was immunodepleted from extracts of serum-treated NIH3T3 cells. After four sequential rounds of immunoprecipitation, the amount of PAK2 in the extract was reduced, on average, by 2-3 fold (FIG. 4C). Treated extracts were then used in kinase assays with the GST-merlin substrate, and activity was determined using SDS-PAGE and autoradiography. As shown in FIG. 4C, extracts immunodepleted for PAK2 (+PAK2 Ab) had a 2-3 fold reduction in kinase activity compared to those treated in a similar fashion with an anti-PAK3 antibody (+PAK3 Ab).

Generation of Merlin Phospho-Specific Antibodies

Figure 5A:
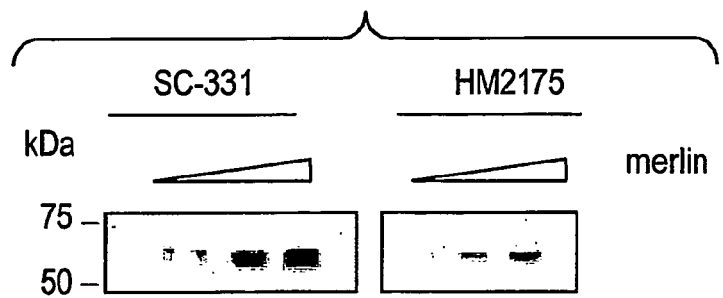
FIGS. 5A-5C illustrate the binding of merlin to phosphoserine 518 antibodies and the subcellular localization of merlin. Western blot analysis was performed on wild-type and S518A merlin expressed in LLC-PK1 cells. "SC-331" denotes commercial antibodies, and "HM2175" denotes phosphospecific antibodies.
Figure 5B:
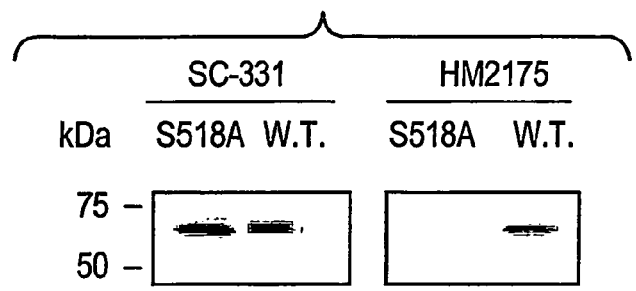

In order to follow the function and localization of merlin phosphorylated at serine 518, antibodies that preferentially recognize the phosphorylated form (HM2175) were produced by employing a chemically-phosphorylated peptide and affinity purification as described herein. To assess the activity of this antisera, ectopically expressed wild-type merlin and merlin S518A were immunoprecipitated with a non-specific merlin antibody (SC331) and then immunoblotted with either SC331 or HM2175. The SC331 antibody detected both the hypo- and hyperphosphorylated form of merlin, while the HM2175 antibody preferentially bound the hyperphosphorylated form of the protein (FIG. 5A). At high concentrations of merlin, HM2175 did recognize the hypophosphorylated form to some extent. When merlin S518A was tested in a similar approach, HM2175 did not recognize the protein, even when loaded at high concentrations (FIG. 5B).

Figure 5C:
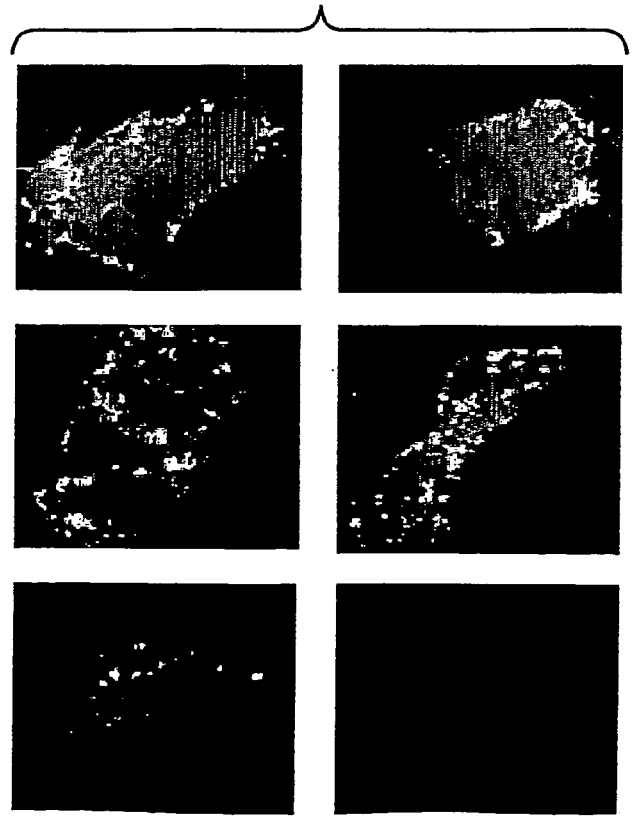

The specificity of the phospho-directed antibodies was tested using immunocytochemistry. LLC-PK1 cells were transfected with vectors expressing either wild-type merlin or the merlin S518A mutant. Fixed cells were then incubated with either the SC331 or HM2175 antibodies. The SC331 antibody recognized both wild-type and mutant merlin (FIG. 5C panels 1 and 2); in contrast, the HM2175 antibody recognized only ectopic wild-type merlin (FIG. 5B panels 5 and 6). This pattern of specificity was observed in many cell lines of both epithelial and fibroblastic origin.

Phosphorylation Leads to Changes in the Subcellular Localization of Merlin in LLC-PK1 Cells To visualize subcellular localization of the different forms of merlin, LLC-PK1 cells were transfected with wild-type merlin or the merlin S518A or S518D mutants and incubated with the SC331 antibody. As shown in FIG. 5B (panel 1), wild-type merlin mainly localized to microvilli. Lower amounts of merlin were present in larger membrane protrusions and in cortical actin structures. Similar results were obtained with the S518A mutant (panel 2). However, the pseudo-phosphorylated mutant of merlin (S518D) was localized predominantly in the larger membrane protrusions (panel 3). This localization was also observed when wild-type merlin was co-transfected with active PAK2 to increase merlin phosphorylation (panel 4). Importantly, the localization of the S518A mutant was not affected by co-transfected PAK2. To validate the observation that merlin relocalization is a result of serine 518 phosphorylation, HM2175 was used to stain cells for phosphorylated merlin. As expected, the HM2175 antibody stained wild-type merlin mainly in the cellular protrusions (panel 5) but did not stain the merlin S518A mutant (panel 6). This result reinforces the conclusion that the phosphorylation of serine 518 is required for the redistribution of merlin and that the redistribution of the merlin 5518D mutant was not simply the consequence of mutating serine 518 to aspartic acid.

Thus, wild-type merlin and the S518A mutant were mostly localized to microvilli and to a small number of protrusions and cortical structures in LLC-PK1 cells. However, when the merlin S518D mutant or wild-type merlin plus PAK2$^{-T402E}$ were introduced into these cells, a marked redistribution of merlin to membrane protrusions was observed. Using the HM2175 antibody to stain both wild-type merlin alone or plus PAK2$^{-402E}$ produced results similar to those obtained using the SC331 antibody. Other modified forms of merlin could not be observed with this antibody. Merlin is not exclusively localized to the protrusions: merlin can be observed in microvilli and cortical actin at a somewhat reduced level. The redistribution is dependent on phosphorylation of serine 518; for example, when merlin S518A was transfected with PAK$_2^-$ $T402E$ the shift in localization was not observed. This redistribution of merlin is highly reminiscent of the redistribution of Ezrin in response to phosphorylation.

Induction of Merlin Phosphorylation by PAK2

Several independent lines of evidence are presented herein which implicate PAK2 as the kinase responsible for inducing phosphorylation of serine 518 on the Nf2 tumor suppressor gene product, merlin. Only PAK2 and PAK3 induced the phosphorylation of the pseudo-substrate in-vitro and the full-length merlin in vivo. We were able to separate PAK2 from PAK3 and demonstrate that merlin-kinase activity migrates in parallel to PAK2. The use of the active PAK2, the dominant negative fragment PAK2-AID, and immunodepeletion of PAK2 directly reinforce the identification of PAK2 as the merlin kinase. Additional circumstantial evidence includes similar kinetics and conditions for PAK2 activation and merlin phosphorylation. The serine 518 site of phosphorylation is similar to many PAK recognition sites such as the phox p47 site (RKRLSQ, SEQ ID NO: 8 vs. MKRLSM, SEQ ID NO: 9) which has been shown to be an in vivo substrate of the PAKs (Knaus et al., Science 269:221-223, 1995 and Ding et al., J. Biol. Chem. 271:24869-24873, 1996). Finally, various kinase inhibitors were tested for their ability to inhibit the activity of the merlin kinase. Staurosporine inhibited the merlin kinase at concentrations in the lower nM range. The inhibitors K252a and K-5720 were inhibitory in the mM range, while H9 had no effect up to a concentration of 1 mM. This inhibition spectrum is in close agreement with previous data regarding PAK inhibition (Zeng et al., J. Cell Sci. 113:471-482,2000 and Yu et al., J. Biochem. (Tokyo) 129:243-251, 2001).

The results of the transfection of cells with mutated forms of Rac reinforces the role of PAK2 in merlin phosphorylation and raises the possibility that additional mechanisms are involved in the regulation of merlin. RacV12K40 and RacV12V37 are defective in signaling towards cytoskeleton and transcriptional events, respectively. In contrast, RacV12K40 activates PAKs but does not induce JNK activation; however, it activates both ROK and POR1, leading to membrane ruffling. In contrast, RacV12V37 activates PAK but does not activate ROK or POR1, thus inducing JNK activation but no membrane ruffling. When cells were transfected with these mutated forms of Rac, merlin was not phosphorylated above basal levels. The fact that RacV12K40 does not induce phosphorylation of merlin further supports the role of PAK2 in the phosphorylation of merlin (Lamarche et al., supra; Joneson et al., supra, and Westwick et al., supra). However, RacV1K37, which can activate PAK, does not induce the phosphorylation of merlin either. This result is consistent with the possibility of multiple Rac-induced pathways for the induction of merlin phosphorylation. This result may also correlate with the inability of the PAK-AID to fully inhibit merlin phosphorylation. As demonstrated for ERMs, multiple effectors can play a role in conformational regulation including phosphorylation and phospholipids (Hirao et al., J. Cell Biol. 135:37-51, 1996 and Matsui et al., supra). Thus, similar multiple effectors may function in the regulation of merlin. The binding of merlin to CD44 has been shown to be enhanced by including phospholipids in the reaction, perhaps by "opening" the structure of merlin and revealing the CD44 interacting domain (Sainio et al., J. Cell Sci. 110: 2249-2260, 1997). Thus, phosphorylation of serine 518 and phospholipids may contribute, concomitantly or sequentially, to the "opening" of merlin. Compared to the efficiency of phosphorylation of full-length merlin, the pseudo-substrate is phosphorylated at a much higher efficiency. This result could be due to the fact that the pseudo-substrate, being out of the context of the full-length protein, is more accessible to PAK2. Similar phenomena have been reported in previous studies looking at the phosphorylation of moesin by Rho-kinase. If desired, the effects of phospholipids on the phosphorylation of merlin can also be examined.

Direct Interaction Between Merlin and PAK

To confirm the functional interaction between merlin and PAK, two different approaches were employed. First, an interaction between merlin and PAK was demonstrated by co-immunoprecipitation from various cell types. NIH3T3 cells were transfected with expression vectors for merlin and one of either PAK1, 2 or 3. Protein extracts were prepared and immunoprecipitated with antibodies against merlin or one of the relevant PAKs. Analysis of the precipitates demonstrated that merlin and either PAK1, 2, or 3 can co-immunoprecipitate. In RT4 cells, a similar result was obtained using antibodies to precipitate endogenous PAK1 or merlin, indicating that these proteins interact.

To examine whether merlin could inhibit PAK activity, the phosphorylation state of merlin was examined under high or low levels of merlin expression. The auto or trans-phosphorylation of PAK1 on serine 144 and serine 423 have been demonstrated as significantly contributing to the activation of PAK1. Hence, detection of an increase in levels of phopspho-PAK1 indicates PAK1 activation (Chong et al., J. Biol. Chem. 276:17347-17353, 2001). Thus, the phosphorylation state of PAK1 was examined in a Rat schwannoma (RT4-D6P2T) cell line harboring an inducible allele of merlin. The RT4D6P2T cell line is derived from the ethylnitrosourea-induced tumor line D6 of the rat peripheral nervous system (Tomozawa Sueoka, Proc Natl Acad Sci, USA 75:6305, 1978). High basal levels of PAK activation are observed in this cell line. The phosphorylation status of PAK1 was examined using standard 2-dimensional protein analysis under conditions of either high or low merlin expression. The basal levels of activated PAK1 were reduced under conditions of high merlin expression compared to conditions of low merlin expression. Thus, merlin reduces the activation of PAK1 in the RT4 cell line.

Based on the physical association between merlin and PAKs and the ability of merlin to inhibit the activation of PAK1, merlin may act as a direct inhibitor of PAKs. Thus, the loss of merlin results in relief of an inhibition on PAK. This effect may result in unregulated activation of PAK, leading to deleterious effects. This mechanism reinforces the usefulness of inhibitors of PAKs as therapeutic agents for the treatment or prevention of cancer, such as Nf2 and other disease in which the Nf2 gene is impaired.

Mechanisms Involving in Regulation of Merlin

The overall picture emerging from these studies is a mechanistically similar approach of regulation between merlin and the ERMs. These proteins are each regulated by multiple mechanisms including phosphorylation and involvement of phospholipids. In both cases, these signals effect the properties of the proteins, including subcellular localization and association with the actin cytoskeleton. There are, however, some major differences between merlin and the ERMs with respect to phosphorylation. First, merlin phosphorylation is induced by the Rac/cdc42 pathway, while ERM phosphorylation seems to be induced in a Rho-dependent fashion. Although there is an extensive network of cross talk among the Rho family of proteins, some functions remain unique to the individual members. The study of the Rho family has focused mainly on their role in regulation of actin dynamics, in which the different family members have different effects (Bishop et al., supra). These differential effects are mediated by separate effectors that interact with the small G-proteins. In the case of merlin, PAK2 is involved; for the ERMs, Rho-kinase and/or PKC-Θ are involved (Pietromonaco et al., J. Biol. Chem. 273:7594-7603, 1998).

Second, the phosphorylation of merlin may render it "inactive" in its growth suppressive role. This hypothesis is supported by experiments in which the head-to-tail association of merlin under phosphorylating conditions was examined. The data suggests that phosphorylation of merlin on serine 518 disrupts merlin self-association (Shaw et al., Developmental Cell 1:63-72, 2001). Taken together with the circumstantial evidence of merlin phosphorylation under growth permissive conditions (Shaw et al., 1998 supra), it is possible that phosphorylation "inactivates" merlin function by opening the protein and disrupting merlin intra- and inter-molecular associations. Additionally, merlin is found in an hypophosphorylated form when the combination of cellular and environmental conditions are growth inhibitory. This inactivation of merlin by phosphorylation is in contrast to the ERMs, where the opening of the proteins is thought to activate the proteins by revealing the actin binding and other protein interaction domains (Bretscher et al., Annu. Rev. Cell Dev. Biol. 16:113-143, 2000 and Pearson et al., Cell 101:259-270, 2000). This difference may or may not be related to the observed difference in association of merlin and the ERMs with the cytoskeleton. While phosphorylation of merlin at serine 518 is required for its dissociation from the cytoskeleton, the opposite is true for ezrin. Phosphorylation of T567 activates ezrin and enhances its association with the cytoskeleton; in contrast, a ezrin T567A mutant is poorly associated (Gautreau et al., surpa).

The fact that immunodepeletion significantly reduces phosphorylation of serine 518 in the in vitro kinase assay implicates PAK2 as directly phosphorylating merlin. The finding that merlin can inhibit Rac induced signaling and that the immediate downstream effector, PAK2, phosphorylates and, perhaps, inactivates merlin reinforces the possibility of the "positive-feedback" mechanism. In such a model, the steady-state role of merlin is to down regulate Rac/cdc41-induced signaling. Once activated, Rac/cdc42 activate PAK2 which in turn phosphorylates merlin and thus relives its inhibitory effect. From a functional point of view, this could be achieved by different mechanisms and impinge of these pathways at different levels (Shaw et al., Developmental Cell 1:63-72, 2001). Merlin could inhibit signaling by acting upstream, by acting upon effectors downstream to Rac/cdc42, or even by both mechanisms. This possibility would not be unprecedented; it has been suggested that activation of ERMs is required for the activation of Rho by LPA and that Rho, in turn, induces phosphorylation of the ERMs (Lamb et al., Nature Cell Biology 2:281-287, 2000). In light of the present data regarding a shift in merlin localization after phosphorylation of serine 518, a model in which merlin controls the subcellular localization of a molecule such as RhoGDI is possible.

It is quite possible that the Rac/cdc42-signaling inhibitory function of merlin is also the tumor suppressor function of merlin, as Rac signaling is necessary for transformation. Many examples exist and are reviewed by Zohn et al. (Oncogene 17:1415-1438, 1998). Rac activation is required for the full transformed phenotype induced by Tiam and Ras (Habets et al., Cell 77:537-749, 1994; Khosravi-Far et al., Mol. Cell Biol. 11:6443-6453, 1995; Qiu et al., Nature 374:457-459, 1995; van Leeuwen et al., Oncogene 11:2215-2221, 1995). Rac has also been shown to regulate cell motility and invasiveness (reviewed by Evers et al., Eur. J. Cancer 36:1269-1274, 2000). Examples include the increased metastatic potential of cells expressing activated Rac (del Posos et al., Oncogene 15:3047-3057, 1997) and the identification of the Rac-GEF, Tiam, as a promoter of invasiveness (Habets et al., supra; Keely et al., Nature 390:632-636, 1997; Shaw et al., Cell 91:949-960, 1997). The fact that Nf2+/−mice have highly metastatic tumors which have a LOH of the wild-type Nf2 allele agrees with the above mentioned possibilities (Ip and Davis, Curr. Opin. Cell Biol. 10:205-219, 1998).

The identification of an established effector of the Rac/cdc42 pathways as the kinase involved in merlin regulation and localization is a strong link between a well-established signaling pathway and a tumor suppressor gene of unknown function. Thus, the Rac/cdc42 pathways play a role in the tumor phenotypes in which the Nf2 gene is involved.

Other Compounds for Inclusion in Individual or Combination Therapies

A variety of compounds may be tested for their ability to decrease PAK kinase activity and/or merlin phosphorylation, such as synthetic organic molecules, naturally occurring organic molecules, nucleic acid molecules, PAK kinase antisense nucleic acids or double stranded RNA molecules, biosynthetic proteins or peptides, naturally occurring peptides or proteins, PAK kinase antibodies, or dominant negative PAK kinase proteins. Additionally, peptides or peptide analogs based on the autoinhibitory regions of PAKs may be used as inhibitors of PAK kinase activity (Maruta et al., Ann. N.Y. Acad. Sci., 886:48-57, 1999). ATP analogs can also be tested for inhibitor activity.

In general, additional drugs for the treatment of cancer may be identified from large libraries of both natural product or synthetic (or semi-synthetic) extracts or chemical libraries according to methods known in the art. Those skilled in the field or drug discovery and development will understand that the precise source of test extracts or compounds is not critical to the methods of the invention.

Accordingly, virtually any number of chemical extracts or compounds can be screened for their effect on PAK kinase activity and/or merlin phosphorylation. Examples of such extracts or compounds include, but are not limited to, plant-, fungal-, prokaryotic- or animal-based extracts, fermentation broths, and synthetic compounds, as well as modification of existing compounds. Numerous methods are also available for generating random or directed synthesis (e.g., semi-synthesis or total synthesis) of any number of chemical compounds, including, but not limited to, saccharide-, lipid-, peptide-, and nucleic acid-based compounds. Synthetic compound libraries are commercially available from Brandon Associates (Merrimack, N.H.) and Aldrich Chemical (Milwaukee, Wis.). Alternatively, libraries of natural compounds in the form of bacterial, fungal, plant, and animal extracts are commercially available from a number of sources, including Biotics (Sussex, UK), Xenova (Slough, UK), Harbor Branch Oceangraphics Institute (Ft. Pierce, Fla.), and PharmaMar, U.S.A. (Cambridge, Mass.). In addition, natural and synthetically produced libraries are produced, if desired, according to methods known in the art, e.g., by standard extraction and fractionation methods. Furthermore, if desired, any library or compound is readily modified using standard chemical, physical, or biochemical methods.

When a crude extract is found to inhibit PAK kinase activity or phosphorylation of merlin, further fractionation of the positive lead extract is necessary to isolate chemical constituent responsible for the observed effect. Thus, the goal of the extraction, fractionation, and purification process is the careful characterization and identification of a chemical entity within the crude extract. Methods of fractionation and purification of such heterogeneous extracts are known in the art. If desired, compounds shown to be useful agents for the treatment of cancer are chemically modified according to methods known in the art. Compounds identified as being of therapeutic value are subsequently analyzed using any standard animal model of cancer known in the art.

Production of Anti-PAK kinase Antibodies for Treating or Preventing Cancer

Anti-PAK kinase antibodies represent exemplary PAK kinase inhibitiors for use in the present invention. Anti-PAK kinase antibodies can be generated using standard methods, such as those described herein. If desired, the ability of an anti-PAK kinase antibody to inhibit PAK kinase activity can be confirmed before the antibody is administered to mammals (e.g., humans) for the treatment or prevention of cancer. For example, standard methods can be used to determine the ability of anti-PAK kinase antibodies to decrease the level of PAK kinase protein, an activity of PAK kinase (e.g., phosphorylation of merlin), the half-life of PAK kinase protein, or the binding of PAK kinase to another molecule. Anti-PAK kinase antibodies can also be tested in animal or primate models, such as those described herein, to measure their effect on cancer in vivo.

For the preparation of polyclonal antibodies reactive with PAK kinase for the treatment or prevention of cancer, one or more PAK kinase proteins, fragments of PAK kinase, or fusion proteins containing defined portions of PAK kinase can be purified from natural sources (e.g., cultures of cells expressing PAK kinase) or synthesized in, e.g., mammalian, insect, or bacterial cells by expression of corresponding DNA sequences contained in a suitable cloning vehicle. Fusion proteins are commonly used as a source of antigen for producing antibodies. The antigenic proteins can be optionally purified, and then coupled to a carrier protein, mixed with Freund's adjuvant to enhance stimulation of the antigenic response in an inoculated animal, and injected into rabbits, mice, or other laboratory animals. Primary immunizations are carried out with Freund's complete adjuvant and subsequent immunizations performed with Freund's incomplete adjuvant. Following booster injections at bi-weekly intervals, the inoculated animals are then bled and the sera isolated. The sera is used directly or is purified prior to use by various methods, including affinity chromatography employing reagents such as Protein A-Sepharose, antigen-Sepharose, and anti-horse-Ig-Sepharose. Antibody titers can be monitored by Western blot and immunoprecipitation analyses using one or more PAK kinases. Immune sera can be affinity purified using PAK kinase coupled to beads. Antiserum specificity can be determined using a panel of proteins, such as PAK kinases and other kinases.

Alternatively, monoclonal antibodies are produced by removing the spleen from the inoculated animal, homogenizing the spleen tissue, and suspending the spleen cells suspended in phosphate buffered saline (PBS). The spleen cells serve as a source of lymphocytes, some of which produce antibody of the appropriate specificity. These cells are then fused with permanently growing myeloma partner cells, and the products of the fusion plated into a number of tissue culture wells in the presence of selective agents, such as hypoxanthine, aminopterine, and thymidine (Mocikat, J. Immunol. Methods 225:185-189, 1999; Jonak et al., Hum. Antibodies Hybridomas 3:177-185, 1992; Srikumaran et al., Science 220:522, 1983). The wells can then be screened by ELISA to identify those containing cells making antibody capable of binding to a PAK kinase, fragments, or mutants thereof. These cells can then be re-plated and, after a period of growth, the wells containing these cells can be screened again to identify antibody-producing cells. Several cloning procedures can be carried out until over 90% of the wells contain single clones that are positive for specific antibody production. From this procedure, a stable line of clones that produce the antibody are established. The monoclonal antibody can then be purified by affinity chromatography using Protein A Sepharose and ion-exchange chromatography, as well as variations and combinations of these techniques. Once produced, monoclonal antibodies are also tested for specific PAK kinase recognition by ELISA, Western blot, and/or immunoprecipitation analysis (see, e.g., Kohler et al., Nature 256:495, 1975; Kohler et al., European Journal of Immunology 6:511, 1976; Kohler et al., European Journal of Immunology 6:292, 1976; Hammerling et al., In Monoclonal Antibodies and T Cell Hybridomas, Elsevier, New York, N.Y., 1981; Ausubel et al., supra).

As an alternate or adjunct immunogen to a PAK kinase, peptides corresponding to relatively unique hydrophilic regions of a PAK kinase can be generated and coupled to keyhole limpet hemocyanin (KLH) through an introduced C-terminal lysine. Antiserum to each of these peptides can be similarly affinity-purified on peptides conjugated to BSA, and specificity tested by ELISA and Western blotting using peptide conjugates, and by Western blotting and immunoprecipitation using a PAK kinase.

Antibodies of the invention are desirably produced using PAK kinase amino acid sequences that do not reside within highly conserved regions, and that appear likely to be antigenic, as evaluated by criteria such as those provided by the Peptide Structure Program (Genetics Computer Group Sequence Analysis Package, Program Manual for the GCG Package, Version 7, 1991) using the algorithm of Jameson et al., CABIOS 4:181, 1988. These fragments can be generated by standard techniques, e.g., by PCR, and cloned into any appropriate expression vector. For example, GST fusion proteins can be expressed in E. coli and purified using a glutathione-agarose affinity matrix (Ausubel et al., supra). To minimize the potential for obtaining antisera that is non-specific or exhibits low-affinity binding to PAK kinase, two or three fusions may be generated for each fragment injected into a separate animal. Antisera are raised by injections in series, preferably including at least three booster injections.

In addition to intact monoclonal and polyclonal anti-PAK kinase antibodies, various genetically engineered antibodies and antibody fragments (e.g., F(ab')2, Fab', Fab, Fv, and sFv fragments) can be produced using standard methods. Truncated versions of monoclonal antibodies, for example, can be produced by recombinant methods in which plasmids are generated that express the desired monoclonal antibody fragment(s) in a suitable host. Ladner (U.S. Pat. Nos. 4,946,778 and 4,704,692) describes methods for preparing single polypeptide chain antibodies. Ward et al., Nature 341:544-546, 1989, describes the preparation of heavy chain variable domain which have high antigen-binding affinities. McCafferty et al. (Nature 348:552-554, 1990) show that complete antibody V domains can be displayed on the surface of fd bacteriophage, that the phage bind specifically to antigen, and that rare phage (one in a million) can be isolated after affinity chromatography. Boss et al. (U.S. Pat. No. 4,816,397) describes various methods for producing immunoglobulins, and immunologically functional fragments thereof, that include at least the variable domains of the heavy and light chains in a single host cell. Cabilly et al. (U.S. Pat. No. 4,816,567) describes methods for preparing chimeric antibodies. In addition, the antibodies can be coupled to compounds, such as toxins or radiolabels.

Assays and Animal Models for Identifying or Testing Compounds of the Invention

Standard kinase assays, such as the in vitro or in vivo PAK kinase assays described herein, can be performed in the presence and absence of one or more candidate compounds to identify compounds that inhibit a PAK kinase (e.g., PAK2). In some embodiments, one or more candidate compounds are administered to a cell, tissue, or animal that has reduced or negligible levels of merlin (Giovannini et al., Genes Dev. 14(13):1617-30, 2000). The reduced levels of merlin may result in a higher initial level of PAK kinase activity and thus facilitate the detection of an inhibition of PAK kinase activity by a candidate compound. Candidate compounds can also be administered to an in vitro sample, cell, tissue, or animal to determine their effect on the phosphorylation of full-length merlin, fragments of merlin, or merlin fusion proteins using standard methods, such as those described herein.

If desired, the compounds of the invention can also be tested for their effect on cancer using standard animal models for neurofibromatosis type 2 (Giovannini et al., supra; McClatchey and Cichowski, Biochim Biophys Acta 1471(2): M73-80, 2001). Additionally, animal models for any other type of cancer (e.g., SCID mouse models) can be used to determine the efficacy of particular compounds or combinations of compounds for treating or preventing cancer.

Administration of Compunds

A compound of the invention may be administered to humans, domestic pets, livestock, or other animals with a pharmaceutically acceptable diluent, carrier, or excipient, in unit dosage form.

The compounds optionally may be administered as pharmaceutically acceptable salts, such as non-toxic acid addition salts or metal complexes that are commonly used in the pharmaceutical industry. Examples of acid addition salts include organic acids such as acetic, lactic, pamoic, maleic, citric, malic, ascorbic, succinic, benzoic, palmitic, suberic, salicylic, tartaric, methanesulfonic, toluenesulfonic, or trifluoroacetic acids or the like; polymeric acids such as tannic acid, carboxymethyl cellulose, or the like; and inorganic acid such as hydrochloric acid, hydrobromic acid, sulfuric acid phosphoric acid, or the like. Metal complexes include zinc, iron, and the like.

The chemical compounds for use in such therapies may be produced and isolated as described herein or by any standard technique known to those in the field of medicinal chemistry. Conventional pharmaceutical practice may be employed to provide suitable formulations or compositions to administer the identified compound to patients suffering from cancer or at increased risk for cancer. Administration may begin before or after the patient is symptomatic.

Any appropriate route of administration may be employed. For example, the therapy may be administered either directly to the tumor (for example, by injection) or systemically (for example, by any conventional administration technique). Administration of the compounds may also be oral, topical parenteral, intravenous, intraarterial, subcutaneous, intramuscular, intracranial, intraorbital, ophthalmalic, intraventricular, intracapsular, intraspinal, intracisternal, intraperitoneal, or intranasal. Alternatively, the compounds may be administered as part of a suppository. Therapeutic formulations may be in the form of liquid solutions or suspensions; for oral administration, formulations may be in the form of tablets or capsules; and for intranasal formulations, in the form of powders, nasal drops, or aerosols. The compounds in a combination therapy may be administered simultaneously or sequentially. The dosage of the therapeutic compounds in a pharmaceutically acceptable formulation depends on a number of factors, including the size and health of the individual patient. The dosage to deliver may be determined by one skilled in the art.

Methods well known in the art for making formulations are found, for example, in "Remington: The Science and Practice of Pharmacy" ((19th ed.) ed. A. R. Gennaro A R., 1995, Mack Publishing Company, Easton, Pa.). Formulations for parenteral administration may, for example, contain excipients, sterile water, saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the compounds. Other potentially useful parenteral delivery systems include ethylene-vinyl acetate copolymer particles, osmotic pumps, implantable infusion systems, and liposomes. Formulations for inhalation may contain excipients, for example, lactose, or may be aqueous solutions containing, for example, polyoxyethylene-9-lauryl ether, glycocholate and deoxycholate, or may be oily solutions for administration in the form of nasal drops, or as a gel.

If desired, treatment with a compound identified according to the methods described above may be combined with more traditional therapies for cancer (e.g., cytotoxic agents, radiation therapy, or surgical removal of cancerous cells).

Other Embodiments

From the foregoing description, it will be apparent that variations and modifications may be made to the invention described herein to adopt it to various usages and conditions.

All publications mentioned in this specification are herein incorporated by reference to the same extent as if each independent publication, patent application, or patent was specifically and individually indicated to be incorporated by reference.

The invention claimed is:

1. A screening method for determining whether a compound may be useful for treating or stabilizing cancer in a mammal, said method comprising measuring PAK kinase activity in the presence and absence of said compound, wherein a decrease in PAK kinase activity is indicative that said compound may be useful to treat or stabilize cancer, wherein said PAK kinase is a polypeptide comprising a sequence at least 90% identical to human PAK2, 3, 4, 5, or 6, and wherein said decrease in PAK kinase activity is determined by identifying decreased phosphorylation of merlin.

2. A screening method for determining whether a compound may be useful for treating or stabilizing cancer in a mammal, said method comprising measuring the phosphorylation level of merlin in a cell in the presence and absence of the compound, wherein a decreased phosphorylation of merlin is indicative that said compound may be useful to treat or stabilize cancer.

3. The method of claim 2, wherein said compound decreases the percentage of merlin that is phosphorylated or the total amount of phosphorylated merlin by at least 50%.

4. The method of claim 1, wherein said compound is a member of a library of at least 5 compounds, all of which are simultaneously administered to a cell.

5. The method of claim 1 or 2, wherein said compound is a PAK kinase antisense nucleic acid or double stranded RNA molecule.

6. The method of claim 1 or 2, wherein said compound is an antibody that specifically binds a PAK kinase.

7. The method of claim 1 or 2, wherein said compound is an ATP analog.

8. The method of claim 1 or 2, wherein said compound reduces the protein level of a PAK kinase.

9. The method of claim 1 or 2, wherein said compound reduces the mRNA level of a PAK kinase.

10. The method of claim 1 or 2, wherein said cancer is neurofibromatosis type 2.

11. The method of claim 1, wherein said PAK kinase is human PAK2 or human PAK3.

12. The method of claim 1, wherein said compound is administered to an in vitro sample.

13. The method of claim 1, wherein said compound is administered to a cell.

14. The method of claim 13, wherein said mammal has cancer or an increased risk for cancer.

15. The method of claim 2 or 13, wherein said cell is in a tissue.

16. The method of claim 2 or 13, wherein said cell is in a mammal.

17. The method of claim 16, wherein said mammal has cancer or an increased risk for cancer.

18. The method of claim 2, wherein said compound is a member of a library of at least 5 compounds, all of which are simultaneously administered to said cell.

* * * * *

UNITED STATES PATENT AND TRADEMARK OFFICE
CERTIFICATE OF CORRECTION

PATENT NO. : 7,514,207 B2 Page 1 of 1
APPLICATION NO. : 10/486750
DATED : April 7, 2009
INVENTOR(S) : Tyler E. Jacks et al.

It is certified that error appears in the above-identified patent and that said Letters Patent is hereby corrected as shown below:

Title Page, (*) Notice: Subject to any disclaimer, the term of this patent is extended or adjusted under 35 U.S.C. 154(b) by 242 days.

should read (*) Notice: Subject to any disclaimer, the term of this patent is extended or adjusted under 35 U.S.C. 154(b) by 729 days.

Signed and Sealed this

Thirteenth Day of April, 2010

David J. Kappos
*Director of the United States Patent and Trademark Office*